United States Patent
Gers-Barlag et al.

(10) Patent No.: US 6,558,683 B2
(45) Date of Patent: *May 6, 2003

(54) EMULSIFIER-FREE FINELY DISPERSED SYSTEMS OF THE OIL-IN-WATER TYPE

(75) Inventors: Heinrich Gers-Barlag, Kummerfeld (DE); Anja Müller, Rümpel (DE)

(73) Assignee: Beiersdorf AG, Hamburg (DE)

( * ) Notice: Subject to any disclaimer, the term of this patent is extended or adjusted under 35 U.S.C. 154(b) by 24 days.

This patent is subject to a terminal disclaimer.

(21) Appl. No.: 10/179,794

(22) Filed: Jun. 25, 2002

(65) Prior Publication Data

US 2003/0017184 A1 Jan. 23, 2003

Related U.S. Application Data

(62) Division of application No. 09/403,682, filed as application No. PCT/EP98/01661 on Mar. 21, 1998, now Pat. No. 6,440,399.

(30) Foreign Application Priority Data

Mar. 25, 1997 (DE) .......................... 197 12 483

(51) Int. Cl.$^7$ .............................. A61K 7/00; A61K 7/42
(52) U.S. Cl. ..................... 424/401; 424/59; 514/937; 514/938; 514/939
(58) Field of Search .................. 424/59, 401; 514/937, 514/938, 939

(56) References Cited

U.S. PATENT DOCUMENTS 5,725,844 A   3/1998   Gers-Barlag et al. ......... 424/59
5,747,012 A   5/1998   Dahms ........................ 424/60

FOREIGN PATENT DOCUMENTS

| DE | 44 25 268 A | 1/1996 |
| EP | 0 610 926 A | 8/1994 |
| EP | 0 680 746 A | 11/1995 |
| EP | 0 823 249 A | 2/1998 |

*Primary Examiner*—Jose' G. Dees
(74) *Attorney, Agent, or Firm*—Norris McLaughlin & Marcus

(57) ABSTRACT

Emulsifier-free cosmetic or dermatological preparations, which are finely dispersed systems of the oil-in-water type, comprising
1. an oil phase,
2. an aqueous phase and
3. one or more types of micronized, inorganic pigments which
   a) have an average particle size of less than 200 nm, and whose particles
   b) have both hydrophilic and lipophilic properties, i.e. have an amphiphilic character, and thus position themselves at the water/oil interface, and which
   c) are selected from the group consisting of metal oxides, which
   d) are optionally coated on the surface and also
optionally comprising further cosmetic or pharmaceutical auxiliaries, additives and/or active ingredients.

10 Claims, 1 Drawing Sheet

W/O Pickering emulsion

EMULSIFIER-FREE FINELY DISPERSED SYSTEMS OF THE OIL-IN-WATER TYPE

This application is a divisional of U.S. Ser. No. 09/403 682, now U.S. Pat. 6,440,399, filed on Feb. 9, 2000, now U.S. Pat. No. 6,440,399 which is a 371 application of PCT/EP98/01661, filed on Mar. 21, 1998.

The present invention relates to emulsifier-free finely dispersed systems of the oil-in-water type, preferably as cosmetic or dermatological preparations.

Emulsions are generally taken to mean hetero-geneous systems which consist of two liquids which are immiscible or have only limited miscibility with one another, which are usually referred to as phases. In an emulsion, one of the two liquids is dispersed in the form of very fine droplets in the other liquid.

If the two liquids are water and oil and if oil droplets are finely dispersed in water, then this is an oil-in-water emulsion (O/W emulsion, e.g. milk). The basic character of a O/W emulsion is defined by the water. In a water-in-oil emulsion (W/O emulsion, e.g. butter), the principle is reversed, the base character here being determined by the oil.

In order to achieve permanent dispersion of one liquid in another, emulsions in the traditional sense require the addition of an interface-active ingredient (emulsifier). Emulsifiers have an amphiphilic molecular structure, consisting of a polar (hydrophilic) and a non-polar (lipophilic) molecular moiety, which are spatially separate from one another. In simple emulsions, finely dispersed droplets of one phase, surrounded by an emulsifier shell, (water droplets in W/O emulsions or lipid vesicles in O/W emulsions) are present in the second phase. Emulsifiers lower the interfacial tension between the phases by positioning themselves at the interface between the two liquids. At the phase boundary, they form oil/water interfacial films, which prevent irreversible coalescence of the droplets. Emulsions are frequently stabilized using emulsifier mixtures.

Traditional emulsifiers can, depending on their hydrophilic molecular moiety, be divided into ionic (anionic, cationic and amphoteric) and nonionic: the most well known example of an anionic emulsifier is soap, which is usually the term used for the water-soluble sodium salts or potassium salts of saturated or unsaturated higher fatty acids. Important examples of cationic emulsifiers are quaternary ammonium compounds. The hydrophilic molecular moiety of nonionic emulsifiers frequently consists of glycerol, polyglycerol, sorbitans, carbohydrates and polyoxyethylene glycols, and, in most cases, is linked to the lipophilic molecular moiety via ester and ether bonds. The lipophilic molecular moiety usually consists of fatty alcohols, fatty acids or isofatty acids. By varying the structure and the size of the polar and nonpolar molecular moiety, the lipophilicity and hydrophilicity of the emulsifiers can be varied within wide limits.

A decisive factor for the stability of an emulsion is the correct choice of emulsifiers. The characteristics of all substances present in the system are to be taken into consideration. In the case of, for example, skin care emulsions, polar oil components and, for example, UV filters lead to instability. As well as the emulsifiers, therefore, other stabilizers are also used which, for example, increase the viscosity of the emulsion and/or act as a protective colloid.

Emulsions are an important type of product in the field of cosmetic and/or dermatological preparations.

Cosmetic preparations are essentially used for skin care. The main aim of skin care in the cosmetics sense is to strengthen or rebuild the skin's natural function as a barrier against environmental influences (e.g. dirt, chemicals, microorganisms) and against the loss of endogenous substances (e.g. water, natural fats, electrolytes). If this function becomes impaired, increased resorption of toxic or allergenic substances or infection by microorganisms may result, leading to toxic or allergic skin reactions.

Another aim of skin care is to compensate for the loss by the skin of grease and water caused by daily washing. This is particularly important if the natural regeneration ability is inadequate. Furthermore, skin care products should protect against environmental influences, in particular against sun and wind, and delay skin ageing.

Cosmetic preparations are also used as deodorants. Such formulations are used to control body odour which is produced when fresh sweat, which is in itself odourless, is decomposed by microorganisms.

Medicinal topical compositions usually comprise one or more medicaments in an effective concentration. For the sake of simplicity, in order to distinguish clearly between cosmetic and medicinal use and corresponding products, reference is made to the legal provisions in the Federal Republic of Germany (e.g. Cosmetics Regulation, Foods and Drugs Act).

The use of customary emulsifiers in cosmetic or dermatological preparations is in itself acceptable. Nevertheless, emulsifiers, like ultimately any chemical substance, may in certain circumstances cause allergic reactions or reactions based on oversensitivity of the user.

For example, it is known that certain light dermatoses are triggered by certain emulsifiers, but also by a variety of fats and simultaneous exposure to sunlight. Such light dermatoses are also called "Mallorca acne". There has thus been no lack of attempts to reduce the amount of customary emulsifiers to a minimum, in the ideal case even to zero.

A reduction in the required amount of emulsifier can, for example, be achieved by taking advantage of the fact that very finely divided solid particles have an additional stabilizing action. The solid substance accumulates at the oil/water phase boundary in the form of a layer, as a result of which coalescence of the dispersed phases is prevented. It is not the chemical properties of the solid particles which are of fundamental importance here, but the surface properties.

Figure 1:
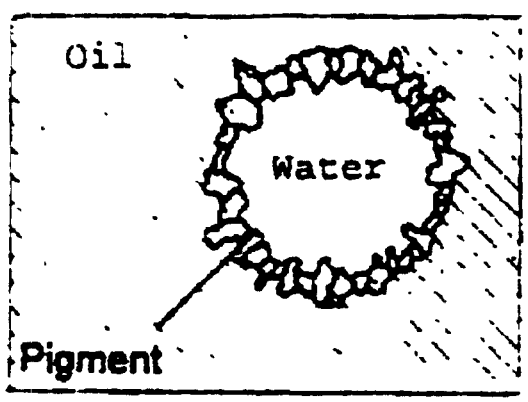
FIG. 1—This depicts a representation of an oil-in-water Pickering emulsion.

Around 1910, Pickering prepared paraffin/water emulsions which were stabilized merely by the addition of various solids, such as basic copper sulphate, basic iron sulphate or other metal sulphates. This type of emulsion is thus also referred to as a Pickering emulsion. For this type of emulsion, Pickering postulated the following conditions:

(1) The solid particles are only suitable for stabilization if they are significantly smaller than the droplets of the inner phase and do not have a tendency to form agglomerates.

(2) An important property of an emulsion-stabilizing solid is also its wettability. I.e. in order to stabilize an O/W emulsion, the solid has, for example, to be more readily wettable by water than by oil.

The original forms of Pickering emulsions initially surfaced, as it were, as undesired secondary effects in a variety of industrial processes, such as, for example, in secondary oil recovery, the extraction of bitumen from tar sand and other separation processes involving two immiscible liquids and fine, dispersed solid particles. These are generally W/O emulsions which are stabilized by mineral solids. Accordingly, investigation of corresponding systems, such as, for example, the oil/water/soot or oil/water/slate dust systems was initially the focus of research activity.

Basic experiments have shown that one characteristic of a Pickering emulsion is that the solid particles are arranged at the interface between the two liquid phases where they form, as it were, a mechanical barrier against the mixing of the liquid droplets.

It is a relatively new technical development to use Pickering emulsions as a base for cosmetic or dermatological preparations.

One way of achieving solids stabilization in a cosmetic or dermatological preparation is, according to May-Alert (*Pharmazie in unserer Zeit* [*Pharmacy in our time*], Vol. 15, 1986, No. 1, 1–7) for example, to use emulsifier mixtures which contain both anionic and cationic surfactants. Since mixing anionic and cationic surfactants produces precipitates of insoluble, electro-neutral compounds, deliberate precipitation of these neutral surfactants in the oil/water interface makes it possible to achieve additional solids stabilization in the sense of a Pickering emulsion.

EP-A-0 686 391 describes water-in-oil emulsions which are free from surface-active ingredients and are stabilized only by solids. Stabilization is achieved here using spherical polyalkylsilsesquioxane particles which have a diameter of from 100 nm up to 20 μm. According to the above, these emulsions can be referred to as Pickering emulsions.

In addition to the described Pickering emulsions, the prior art describes further emulsifier-free, finely dispersed cosmetic or dermatological preparations which are generally referred to as hydrodispersions. Hydrodispersions are dispersions of a liquid, semi-solid or solid internal (discontinuous) lipid phase in an outer aqueous (continuous) phase. Hydrodispersions, like other emulsions, are metastable systems and therefore have a tendency to convert into a state of two mutually coherent discrete phases.

In the case of hydrodispersions of a liquid lipid phase in an outer aqueous phase, stability can be ensured, for example, by constructing, in the aqueous phase, a gel structure in which the lipid droplets are stably suspended. DE-A 44 25 268 describes stable finely dispersed, emulsifier-free cosmetic or dermatological preparations of the oil-in-water type, which, in addition to one oil phase and one water phase, comprise one or more thickeners from the group consisting of acrylic polymers, polysaccharides and alkyl ethers thereof, where these thickeners must not cause any lowering of the interfacial tension.

The object of the present invention was to extend the prior art to include cosmetic or dermatological preparations of the oil-in-water type, in which it is not necessary to use any emulsifiers of a conventional type.

Surprisingly, this object is achieved by emulsifier-free cosmetic or dermatological preparations which are finely dispersed systems of the oil-in-water type, comprising 1. an oil phase,
2. an aqueous phase and
3. one or more types of micronized, inorganic pigments which
   a) have an average particle size of less than 200 nm, and whose particles
   b) have both hydrophilic and lipophilic properties, i.e. have an amphiphilic character, and thus position themselves at the water/oil interface, and which
   c) are selected from the group consisting of metal oxides, which
   d) are optionally coated on the surface and also optionally comprising further cosmetic or pharmaceutical auxiliaries, additives and/or active ingredients.

The amphiphilic character of the inorganic pigments according to the invention is evident, for example, from the fact that the latter are dispersible both in water and in oil.

German laid-open specification 43 03 983 discloses cosmetic or dermatological light protection formulations which are based on hydrodispersions and comprise inorganic micropigments as UV filter substances, the formulations consisting of an inner lipid phase and an outer aqueous phase and being essentially free from emulsifiers. However, the inorganic micropigments are incorporated into the lipid phase of the hydrodispersion and act as UV absorbers or UV reflectors. This prior art document was therefore unable to indicate the route to the present invention.

The preparations according to the invention are mixtures of oils or oil-soluble substances and water or water-soluble components, which are stabilized by adding micronized solids particles and which do not contain an emulsifier in the traditional sense. One way of explaining the stability of these preparations is that the pigment particles—as shown diagrammatically in FIG. 1—attach themselves to the droplets of the disperse phase and form, as it were, a mechanical barrier, which prevents coalescence of the droplets.

The preparations according to the invention are extremely satisfactory preparations in every respect, whose aqueous/fatty phase ratio can be varied within extraordinarily wide limits and, in addition, have the advantage over the prior art that large amounts of oils can be stably incorporated in water.

The fatty phase content of the formulations according to the invention is preferably chosen from the range of from 0.5 to 75% by weight, based on the total weight of the formulations.

It is advantageous to choose the average particle diameter of the pigments used to be between 1 nm and 200 nm, particularly advantageously between 5 nm and 100 nm.

It is essentially insignificant for the present invention in which of the potentially naturally occurring modifications the metal oxides are present.

It is advantageous for the purposes of the present invention to stabilize Pickering emulsions using untreated, virtually pure pigment particles, in particular those which can also be used as dye in the food industry and/or as absorber of UV radiation in sun-screens. Examples of advantageous pigments are titanium dioxide pigments and/or zinc oxide pigments, which are available under the trade names KRONOS® 1171 ($TiO_2$) from Kronos Titan, as well as zinc oxide neutral from Haarmann & Reimer and NanoX (ZnO) from Parcros Chemical Group.

For the purposes of the present invention, Pickering emulsions are advantageously stabilized by inorganic pigments which have been surface-treated (coated) to repel water, it being the intention that the amphiphilic character is simultaneously formed or retained. This surface-treatment may involve providing the pigments with a thin hydrophobic layer by processes known per se.

One such process, which is described below using titanium dioxide as an example, consists in, for example, producing the hydrophobic surface layer according to the following reaction

$$n TiO_2 + m(RO)_3Si\text{—}R' \rightarrow n TiO_2(\text{surf.})$$

n and m are arbitrary stoichiometric parameters, and R and R' are the desired organic radicals. Particularly advantageous pigments are TiO$_2$ pigments, for example those coated with aluminium stearate and available under the trade name MT 100 T from TAYCA.

Another advantageous coating of the inorganic pigments consists of dimethylpolysiloxane (also: dimethicone), a mixture of completely methylated, linear siloxane polymers which have been terminally blocked with trimethylsiloxy units. Zinc oxide pigments which have been coated in this way are particularly advantageous for the purposes of the present invention.

It is also advantageous to coat the inorganic pigments with a mixture of dimethylpolysiloxane, in particular dimethylpolysiloxane having an average chain length of from 200 to 350 dimethylsiloxane units, and silica gel which is also referred to as simethicone. It is particularly advantageous for the inorganic pigments to be additionally coated with aluminium hydroxide or aluminium oxide hydrate (also: alumina, CAS No.: 1333-84-2). Titanium dioxides which have been coated with simethicone and alumina are particularly advantageous, in which case the coating can also comprise water. One example thereof is the titanium dioxide obtainable under the trade name Eusolex T2000 from Merck.

For the purposes of the present invention, Pickering emulsions are also particularly advantageously stabilized by metal oxide particles coated with aluminium hydroxide and/or silicon dioxide. Advantageous examples are titanium dioxide particles which are available under the name EUSO-LEX® TA from Merck.

In all of the above cases it is advantageous to choose the concentration of the pigments to be greater than 0.1% by weight, particularly advantageously between 0.1% and 30% by weight, based on the total weight of the preparations.

The Pickering emulsions according to the invention can be used as bases for cosmetic or dermatological formulations. These can have the customary composition and be used, for example, for the treatment and care of the skin, as lip care product, as deodorant and as make-up or make-up remover product in decorative cosmetics or as light protection preparation. For use, the cosmetic and dermatological preparations according to the invention are applied to the skin in sufficient amount in the manner customary for cosmetics.

Accordingly, for the purposes of the present invention, cosmetic or topical dermatological compositions may, depending on their structure, be used, for example, as skin-protection cream, cleansing milk, sun-screen lotion, nutrient cream, day or night cream, etc. Where appropriate, it is possible and advantageous to use the compositions according to the invention as bases for pharmaceutical formulations.

The cosmetic and dermatological preparations according to the invention may comprise cosmetic auxiliaries, as customarily used in such preparations, e.g. preservatives, bactericides, perfumes, antifoams, dyes, pigments which have a colouring effect, thickeners, plasticizers, moisturizing and/or moisture-retaining substances, fats, oils, waxes or other customary constituents of a cosmetic or dermatological formulation, such as alcohols, polyols, polymers, foam stabilizers, electrolytes, organic solvents or silicone derivatives.

Pickering emulsions according to the invention may advantageously also comprise thickeners to improve the tactile properties of the emulsion and/or to establish a suitable viscosity. Examples of advantageous thickeners are starch derivatives, cellulose derivatives, carbopols, xanthan gum and phyllosilicates. The use of hydroxyethylcellulose, which is available, for example, under the trade name NATROSOL PLUS 330 CS from Aqualon, is particularly advantageous.

In particular, the Pickering emulsions according to the invention may also comprise antioxidants. According to the invention, favourable antioxidants which can be used are any antioxidants suitable or conventional for cosmetic and/or dermatological applications.

The antioxidants are advantageously selected from the group consisting of amino acids (e.g. glycine, histidine, tyrosine, tryptophan) and their derivatives, imidazoles, (e.g. urocanic acid) and their derivatives, peptides, such as D,L-carnosine, D-carnosine, L-carnosine and their derivatives (e.g. anserine), carotenoids, carotenes (e.g. α-carotene, β-carotene, lycopene) and their derivatives, chlorogenic acid and its derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximines) in-very low tolerated doses (e.g. pmol to µmol/kg) , and also (metal) chelating agents (e.g. α-hydroxyfatty acids, palmitic acid, phytic acid, lactoferrin) , α-hydroxy acids (e.g. citric acid, lactic acid, malic acid), humic acid, bile acid, bile extracts, bilirubin, biliverdin, EDTA, ECTA and their derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin, rutinic acid and its derivatives, α-glycosylrutin, ferulic acid, furfurylideneglucitol, carnosine, butylated hydroxytoluene, butylated hydroxyanisole, nordihydroguaiac acid, nordihydroguaiaretic acid, trihydroxybutyrophenone, uric acid and its derivatives, mannose and its derivatives, zinc and its derivatives (e.g. ZnO, ZnSO$_4$), selenium and its derivatives (e.g. selenomethionine), stilbenes and their derivatives (e.g. stilbene oxide, trans-stilbene oxide), and the derivatives (salts, esters, ethers, sugars, nucleotides, nucleosides, peptides and lipids) of said active ingredients which are suitable according to the invention.

The amount of the abovementioned antioxidants (one or more compounds) in the preparations according to the invention is preferably from 0.001 to 30% by weight, particularly preferably from 0.05 to 20% by weight, in particular 1–10% by weight, based on the total weight of the preparation.

If vitamin E and/or its derivatives are used as the antioxidant or antioxidants, their respective concentrations are advantageously chosen from the range of 0.001–10% by weight, based on the total weight of the formulation.

If vitamin A or vitamin A derivatives or carotenes or their derivatives are used as the antioxidant or antioxidants, their respective concentrations are advantageously chosen from the range of 0.001–10% by weight, based on the total weight of the formulation.

Cosmetic and dermatological preparations which are in the form of a sunscreen are also favourable. These preferably comprise at least one UV-A filter substance and/or at least one UV-B filter substance and/or at least one further inorganic pigment selected from the group consisting of the oxides of iron, zirconium, silicon, manganese, aluminium, cerium and mixtures thereof and also modifications in which the oxides are the active agents.

For the purposes of the present invention, it is, however, also advantageous to provide such cosmetic and dermatological preparations whose main purpose is not protection against sunlight, but which nevertheless comprise substances which protect against UV. For example, UV-A and UV-B filter substances are commonly incorporated into day cream.

The preparations according to the invention can advantageously comprise further substances which absorb UV radiation in the UV-B range, the total amount of filter substances being, for example, from 0.1% by weight to 30% by weight, preferably from 0.5 to 10 by weight, in particular from 1 to 6% by weight, based on the total weight of the preparations, in order to provide cosmetic preparations which protect the hair and/or the skin from the whole region of ultraviolet radiation.

If the emulsions according to the invention contain UV-B filter substances, the latter may be oil-soluble or water-soluble. Examples of oil-soluble UV-B filters which are advantageous according to the invention are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino) benzoate;

Esters of cinnamic acid, preferably 2-ethylhexyl 4-methoxycinnamate, isopentyl 4-methoxycinnamate;

Esters of salicylic acid, preferably 2-ethylhexyl salicylate, 4-isopropylbenzyl salicylate, homo-menthyl salicylate;

Derivatives of benzophenone, preferably 2-hydroxy-4-methoxybenzophenone, 2-hydroxy-4-methoxy-4'-methylbenzophenone, 2,2'-dihydroxy-4-methoxybenzophenone;

Esters of benzalmalonic acid, preferably di(2-ethylhexyl) 4-methoxybenzalmalonate, 2,4,6-tri-anilino(p-carbo-2'ethyl-1'-hexyloxy)-1,3,5-triazine.

Examples of advantageous water-soluble UV-B filters are:

Salts of 2-phenylbenzimidazole-5-sulphonic acid, such as its sodium, potassium or its triethanolammonium salt, and also the sulphonic acid itself;

Sulphonic acid derivatives of benzophenones, preferably 2-hydroxy-4-methoxybenzophenone-5-sulphonic acid and its salts;

Sulphonic acid derivatives of 3-benzylidenecamphor, such as e.g. 4-(2-oxo-3-bornylidenemethyl)benzene-sulphonic acid, 2-methyl-5-(2-oxo-3-bornylidenemethyl)sulphonic acid and their salts.

The list of said UV-B filters, which may be used in the Pickering emulsions according to the invention, is of course not intended to be limiting.

It can also be advantageous to use, in the Pickering emulsions according to the invention, UV-A filters which have hitherto been customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. Preparations which contain the UV-A filters are also provided by the invention. The amounts which may be used are as for the UV-B combination.

Preparations according to the invention can also be advantageously used as bases for cosmetic deodorants and antiperspirants, so that a particular embodiment of the present invention relates to Pickering emulsions as bases for cosmetic deodorants.

Cosmetic deodorants are used to control body odour which arises when fresh sweat, which is in itself odourless, is decomposed by microorganisms. Customary cosmetic deodorants are based on various modes of action.

In antiperspirants, astringents, mainly aluminium salts, such as aluminium hydroxychloride (aluchlorhydrate), reduce sweat production.

The use of antimicrobial substances in cosmetic deodorants can reduce the bacterial flora of the skin. In an ideal situation, only the microorganisms which cause the odour should be effectively reduced. The flow of sweat itself is not influenced as a result, and in ideal circumstances, only microbial decomposition of sweat is stopped temporarily.

The combination of astringents and antimicrobial substances in one and the same composition is also common. Antimicrobial substances are electrolytes and strong Lewis acids, and the incorporation of relatively large amounts of electrolytes and/or Lewis acids into cosmetic and/or dermatological preparations is generally not without problems. Surprisingly, the Pickering emulsions according to the invention are stable even when relatively high concentrations of such active ingredients are used.

O/W Pickering emulsions according to the invention are obtainable by firstly dispersing the pigments in the aqueous phase and then combining the aqueous phase with the fatty phase. Dispersing the pigments firstly in the fatty phase usually gives W/o Pickering emulsions.

The invention thus also provides a process for the preparation of the Pickering emulsions according to the invention, which is characterized in that the amphiphilic inorganic pigments are dispersed in a manner known per se in the aqueous phase, which, if desired, comprises cosmetic or pharmaceutical auxiliaries, additives and/or active ingredients, with uniform stirring and, where necessary, with heating, and during the homogenization process the preferably liquid fatty phase, which, if desired, likewise comprises cosmetic or pharmaceutical auxiliaries, additives and/or active ingredients, is mixed with the aqueous phase.

The following examples serve to illustrate the present invention, without limiting it. The numerical values in the examples indicate percentages by weight, based on the total weight of the respective preparations.

EXAMPLES

Example 1

| Mineral oil | 34 |
| Caprylic/capric triglyceride | 34 |
| TiO$_2$ (EUSOLEX ® TA) | 3 |
| Butylene glycol | 3 |
| Water | ad 100 |

Example 2

| Mineral oil | 20 |
| Caprylic/capric triglyceride | 20 |

-continued

| | |
|---|---|
| TiO₂ (EUSOLEX ® T2000) | 5 |
| Glycerol | 3 |
| Butylmethoxydibenzoylmethane | 2 |
| Methylbenzylidenecamphor | 2 |
| Octyltriazone | 1 |
| Cetylhydroxyethylcellulose | 0.5 |
| Water | ad 100 |

Example 3

| | |
|---|---|
| Mineral oil | 33 |
| Caprylic/capric triglyceride | 33 |
| Glycerol | 3 |
| TiO₂ (EUSOLEX ® TA) | 2.5 |
| Thickener | 2.5 |
| Water | ad 100 |

Example 4

| | |
|---|---|
| Caprylic/capric triglyceride | 10 |
| Mineral oil | 5 |
| TiO₂ (EUSOLEX ® TA) | 3 |
| Glycerol | 3 |
| Thickener | 0.5 |
| Water | ad 100 |

Example 5

| | |
|---|---|
| Caprylic/capric triglyceride | 66 |
| TiO₂ (KRONOS ® 1171) | 5 |
| Glycerol | 3 |
| Water | ad 100 |

Example 6

| | |
|---|---|
| Caprylic/capric triglyceride | 30 |
| Octyl salicylate | 5 |
| TiO₂ (KRONOS ® 1171) | 3 |
| Glycerol | 3 |
| Zinc oxide | 2.5 |
| Butylmethoxydibenzoylmethane | 2 |
| Methylbenzylidenecamphor | 2 |
| Octyltriazone | 1 |
| Octyl methoxycinnamate | 1 |
| Water | ad 100 |

Example 7

| | |
|---|---|
| Caprylic/capric triglyceride | 20 |
| Methylbenzylidenecamphor | 4 |
| Glycerol | 3 |
| Zinc oxide | 2.5 |
| Butylmethoxydibenzoylmethane | 2 |
| Octyltriazone | 2 |

-continued

| | |
|---|---|
| Thickener | 0.5 |
| Water | ad 100 |

Example 8

| | |
|---|---|
| Caprylic/capric triglyceride | 66 |
| Glycerol | 3 |
| TiO₂ (KRONOS ® 1171) | 2.5 |
| Thickener | 2.5 |
| Water | ad 100 |

Example 9

| | |
|---|---|
| Caprylic/capric triglyceride | 22 |
| Mineral oil | 11 |
| Zinc oxide | 3 |
| Butylene glycol | 3 |
| Cetylhydroxyethylcellulose | 0.5 |
| Water | ad 100 |

What is claimed is:

1. An emulsifier-free cosmetic or dermatological preparation, which preparation is a finely dispersed oil-in-water system, said preparation comprising a) an oil phase;

b) an aqueous phase; and c) micronized, inorganic pigments particles positioned at an interface of said oil phase and said aqueous phase, said micronized, inorganic pigment particles being metal oxides which:
   i) have an average particle size of less than 200 nm;
   ii) have both hydrophilic and lipophilic properties resulting in an amphiphilic character; and d) optionally cosmetic or pharmaceutical auxiliaries, additives and/or active substances.

2. Preparation according to claim 1, wherein the content of the inorganic pigments used is between 0.1% by weight and 30% by weight, based on the total weight of the preparation.

3. Preparation according to claim 1, wherein the particle diameter of the inorganic pigments used is between 5 nm and 100 nm.

4. Preparation according to claim 1, wherein the inorganic pigments used are titanium dioxide and/or zinc oxide.

5. Preparation according to claim 1, wherein the inorganic pigments used have been surface-treated to repel water, the amphiphilic character of the pigments being formed or retained.

6. Preparation according to claim 1, wherein the inorganic pigments used are titanium dioxide particles coated with simethicone and alumina.

7. Preparation according to claim 1, comprising one or more additives or active ingredients selected from the group consisting of antioxidants and/or UV protectants.

8. Preparation according to claim 1, comprising one or more additives or active ingredients selected from the group consisting of astringents and/or antimicrobial substances.

9. A process for preparing the emulsifier-free cosmetic or dermatological preparation of claim 1, said process comprising:

a) dispersing an amphiphilic inorganic metal oxide pigment in an oil phase to form a mixture of said amphiphilic inorganic metal oxide pigment and said oil phase, said oil phase optionally comprising one or more cosmetic or pharmaceutical auxiliaries, additives and/or active ingredients;

b) homogenizing said mixture by uniform stirring and, optionally, heating; and c) during said homogenizing, mixing an aqueous phase with said mixture, said aqueous phase also optionally comprising one or more cosmetic or pharmaceutical auxiliaries, additives and/or active ingredients.

10. A method of caring for skin, said method comprising applying to skin a preparation according to any one of claims 1–9.

* * * * *